(12) United States Patent
Thomas et al.

(10) Patent No.: US 6,329,414 B1
(45) Date of Patent: *Dec. 11, 2001

(54) HISTIDINE CONTAINING NUTRICEUTICAL

(75) Inventors: Peter G. Thomas, Charlottesville, VA (US); A. Michael Wade, Mebane, NC (US)

(73) Assignee: Cytos Pharmaceuticals LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/393,891

(22) Filed: Sep. 10, 1999

Related U.S. Application Data

(63) Continuation of application No. 08/962,655, filed on Nov. 3, 1997, now Pat. No. 5,972,985.

(51) Int. Cl.[7] .................. A61K 31/415; A61K 31/12; A61K 31/07; A61K 31/015
(52) U.S. Cl. .................. 514/400; 514/691; 514/725; 514/763
(58) Field of Search .................. 514/400, 458, 514/763, 474, 691, 725

(56) References Cited

U.S. PATENT DOCUMENTS 4,025,645 * 5/1977 Jelenko, III .
5,336,616 * 8/1994 Livesey et al. .

* cited by examiner

*Primary Examiner*—William R. A. Jarvis
(74) *Attorney, Agent, or Firm*—Isaac Angres; Susan Petraglia

(57) ABSTRACT

Nutriceutical compositions useful as a dietary supplement which have antioxidant/free radical scavengers and also having a cytoprotective effect are disclosed. The compositions contain a cytoprotective and antioxidant/free radical scavenging amount of at least one of D-histidine, L-histidine, a racemic mixture thereof, a non-racemic mixture thereof, and nutriceutically acceptable salts thereof in combination with phytonutrients having antioxidant properties such as canthanaxin, vitamin A and limonene. The compositions can be prepared in capsule form, tablets, sustained release tablets, suspensions and oral rehydration solutions.

3 Claims, No Drawings

HISTIDINE CONTAINING NUTRICEUTICAL

This application is a continuation of application Ser. No. 08/962,655 filed Nov. 3, 1997 which application is now U.S. Pat. No. 5,972,985.

FIELD OF THE INVENTION

The present invention relates to compositions of matter in the field of nutriceuticals, phytochemicals, and phytonutrients. More in particular, the present investigation relates to dietary supplements which incorporate cytoprotective agents, free radical scavengers and antioxidants. The instant invention is also directed to antioxidant formulations and vitamin supplements which incorporate histidine as an antioxidant, as a free radical scavenger and as a cytoprotective agent. The invention also provides compositions that scavenge singlet oxygen. The present invention also provides sustained release formulations containing histidine as well as histidine in combination with antioxidants and other nutrients and micronutrients. The instant invention also provides a method for providing nutrition to a mammal in need thereof by administering histidine in combination with other vitamin supplements.

BACKGROUND OF THE INVENTION

When free radicals attack biological cells and tissues they can be incredibly destructive. They damage our cells, which can mean premature aging, reduced immune function, inflammation and ultimately degenerative disease. Among our primary defenses are the antioxidant nutrients, of which the most well known are vitamins C and E. The biological activity of antioxidants is enormously important to our health. Antioxidants have been known to neutralize free radical damage, rendering them all but harmless. Aging and deterioration in human cells is caused by the chemical process of oxidation. Scientists theorize that when pollutants, chemicals, and toxins such as cigarette smoke or food additives combine with oxygen in your bloodstream, they produce unstable (and harmful) molecules called "free radicals". Free radicals cause cells to die off faster than your body can produce new ones. As you get older, your body produces fewer new cells to replace the ones that die. This combination results in the aging process. When free radicals attack human cells, they weaken cell walls and erode them to the core. These weakened cells age rapidly, inviting disease and infection because of their unhealthy state. Scientists have identified a group of vitamins called antioxidants which choke off the supply of oxygen to the free radicals, thereby rendering them almost harmless. With free radicals thus neutralized, human cells and tissue remain younger and healthier.

The term nutriceutical appears to have been introduced initially by Stephen de Felice, M.D., director of New York's Foundation for Innovation in Medicine. The term nutriceutical is intended to describe specific chemical compounds found in foods that may prevent disease. The term phytochemical is a more recent evolution of the term that emphasizes the plant source of most of these protective, disease-preventing compounds. A true nutritional role for phytochemicals is becoming more probable every day as research uncovers more of their remarkable benefits. In fact, the term phytonutrient better describes the compounds' status. Someday, phytochemicals may indeed be classified as essential nutrients. A significant body of research suggests a strong link between diet and health. Current studies are showing that as we move away from the diet of our ancestors we succumb to modern diseases. Evidence of this can be seen in societies such as the centenarian tribes that live in remote villages in the Andes mountains and who still embrace traditional dietary practices. These people have been reported to live extraordinarily long lives that are free of such illnesses as cancer, heart disease and arthritis. Since few people in our modern society live today as do the tribes in remote Andean villages, researchers have examined epidemiological evidence from modern societies for clues to the diet-disease connection. On the basis of such studies, biochemical researchers have identified certain phytochemicals that aid the body in maintaining health and combating disease. As an overall guideline, health authorities recommend that we consume diets rich in whole grains and fresh fruits and vegetables as well as reduce fat and animal-protein consumption.

The amino acid L-histidine having the chemical structure shown below

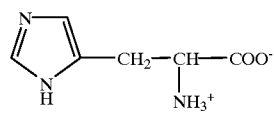

is one of the 10 essential amino acids which cannot be synthesized by the human body and therefore must be obtained by the diet. In addition to histidine's routine metabolic role as a protein building block, histidine is an effective scavenger of toxic oxygen species and therefore is useful in the protection of cells and tissues from a variety of inflammatory disease processes.

Several in vitro and in vivo laboratory studies have demonstrated histidine's antioxidant effects. The antioxidant effect observed with histidine has been attributed to its ability to scavenge highly reactive oxygen species, particularly singlet oxygen ($^1O_2$) and hydroxyl radical (.OH) produced by the degradation of hydrogen peroxide and molecular oxygen. In one study [A. K. Vinnikova et al "Singlet Oxygen-induced inhibition of cardiac sarcolemmal $Na^+K^+$-ATPase", J. Mol. Cell. Card., 24: 465–470 (1992) and R. C. Kureja et al "Singlet oxygen interaction with $Ca^{2+-}$ ATPase of cardiac sarcoplasmic reticulum"; Circ. ReS. 69, 1003–1014 (1991)], histidine afforded dose-dependent protection to sarcolemmal $Na^+$-$K^+$-ATPase and $Ca^{2+}$-ATPase subjected to singlet oxygen-mediated damage in vitro. The researchers of the above studies compared the effects of histidine, superoxide dismutase (SOD) and catalase in sarcoplasmic is reticulum preparations and noted that histidine was efficient at protecting the enzymes' integrity due to its unique ability to scavenge singlet oxygen species. In another study [M. A. Khalid et al "Histidine protects bovine endothelial cells against anoxia reoxygenation injury by scavenging singlet oxygen"; Circulation, 86: I223 (1992)] bovine endothelial cells treated with histidine were protected from post-anoxic reoxygenation injury.

Other studies [A. K. Vinnikova et al "Singlet Oxygen-induced inhibition of cardiac sarcolemmal $Na^+K^+$-ATPase", J. Mol. Cell. Card., 24: 465–470 (1992); Q. Cai et al "Antioxidative properties of histidine and its effect on myocardial injury during ischemia reperfusion in isolated rat heart", J. Cardiovasc. Pharmacol.; 25: 147–155 (1995); R. C. Kukreja et al "Protective effects of histidine during ischemia-reperfusion in isolated perfused rat hearts", Am. J. Physiol., 264:H1370–H1381 (1993) and R. C. Kukreja et al "The oxygen free radical system: from equation through membrane-protein interactions to cardiovascular injury and protection", *Cardiovasc. Res.* 26: 641–655 (1992)] have shown that canine and rodent heart preparations subjected to ischemia/reperfusion injury were protected from singlet, hydroxyl radical and superoxide anion damage by the application of L-histidine.

Recent in vivo studies in rats subjected to coronary artery ligation and reperfusion demonstrated that 3 mM histidine could reduce ventricular infarcts and the duration and severity of arrhythmias, and was more effective than superoxide dismutase at achieving this protectant effect.

In applicants pending U.S. application Ser. No. 08/718, 705 filed Sep. 27, 1996, it is disclosed that histidine has a strong protective effect against intestinal fluid accumulation induced by both Salmonella infection and by cholera toxin in a mouse model. *S. typhimurium*-induced intestinal fluid accumulation was reduced 47% in histidine-treated mice, and evaluation of tissues by light and electron microsocopy showed significant protection of the intestinal mucosa by histidine. In addition, mean cholera toxin-induced intestinal fluid accumulation was reduced 54% in histidine-treated mice. The fact that these two diarrhea-inducing agents act by different mechanisms indicates that histidine's intestinal protective effects may be very broad.

In a study dealing with mechanism of action [M. C. Erikson et al, "Influence of histidine on lipid peroxidation in sarcoplasmic reticulum"; *Arch. Biochem. Biophys.* 292: 427–432 (1992)], the effects of histidine on lipid peroxidation in an in vitro system derived from fish muscle sarcoplasnic reticulum were shown to be dependent on the order of addition of components (histidine, ferric iron, and reduced nicotinamide-adenine-dinucleotide). The studies by Erikson et al suggest that histidine's protective effect in vivo may be related to its ability to interfere with the reduction of ferric iron. Ginsburg [I. Ginsburg, "Cationic polyelectrolytes: Potent opsonic agents which activate the respiratory burst in leukocytes"; *Free Radic. Res. Commun.* 8:11–26 (1989)] has shown that polyhistidine or histidine complexed to the free radical scavengers, SOD or catalase, enhanced their ability to function as intracellular antioxidants. In vitro and in vivo studies [A. A. Boldyrev, "Natural histidine-containing dipeptide carnosine as a potent hydrophilic antioxidant with membrane stabilizing function"; *Mol. Chem. Neuropathol.*, 19: 185–192 (1993) and O. V. Naumova et al; "Effect of carnosine on liver enzyme systems of animals subjected to radiation"; *Biokhimiya*, 57: 1373–1377 (1992] with the dipeptide carnosine (β-Alanine-L-histidine) indicated that its radioprotective and membrane stabilizing effects were attributed to the actions of histidine, not alanine. Camosine functions as a pH buffer and as a chelator of a variety of metals, which contributes to its oxygen scavenging profile.

The prior art is silent regarding nutriceuticals and/or dietary supplements containing histidine as a cytoprotective agent and as an antioxidant/free radical scavenging agent. Furthermore, the prior art is silent on nutriceuticals and/or dietary supplements incorporating histidine as a scavenger of singlet oxygen. The present invention provides nutriceutical formulations incorporating histidine as an antioxidant/free radical scavenger and therefore fills a long-felt need not currently available in the market place.

ADVANTAGES OF THE INVENTION

A primary advantage of the present invention is to provide nutraceutical compositions incorporating cytoprotective agents.

An additional advantage of the present invention is to provide nutraceutical compositions incorporating histidine as a cytoprotective agent.

Another important advantage of the present invention is to provide histidine containing antioxidant/free radical scavenging dietary supplement formulations.

A further advantage of the invention is to provide dietary supplements incorporating antioxidants in combination with cytoprotective agents.

Another advantage of the present invention is to provide compositions containing histidine and antioxidants and being capable of efficiently scavenging singlet oxygen providing a complementary protective effect.

A still further advantage of the invention is to provide vitamin formulations incorporating histidine as a cytoprotective agent.

An additional advantage of the present invention is to provide sustained release formulations of histidine in combination with antioxidants and vitamins.

A further advantage of the invention is to provide soft gelatin shell vitamin formulations incorporating histidine as a cytoprotective agent.

Other advantages will become apparent as further described below in the preferred embodiments of the present invention.

SUMMARY OF THE INVENTION

Briefly, the present invention is directed to a nutriceutical composition comprising: (a) an effective amount of a cytoprotective agent; and (b) an effective amount of one or more of a group of phytonutrients having antioxidant activity.

In another aspect, the present invention relates to an antioxidant dietary supplement comprising: (a) an effective amount of histidine; (b) an effective amount of ascorbic acid; and (c) an effective amount of alpha-tocopherol.

The instant invention is also directed to a dietary supplement comprising: (a) an effective amount of a synthetic or naturally occurring vitamin or mixtures thereof; and (b) an effective cytoprotective amount of histidine.

The invention also provides a method of providing nutrition to a mammal in need thereof, which method comprises administering to said mammal a composition comprising: (a) an effective amount of a cyto-protective agent wherein said cyto-protective agent is selected from the group consisting of at least one of D-histidine, L-histidine, a racemic mixture thereof, a non-racemic mixture thereof, and nutriceutically acceptable salts thereof; and (b) an effective amount of at least one of a phytonutrient having antioxidant activity wherein said phytonutrient having antioxidant activity is selected from the group consisting of carotenoids, flavonoids, tocopherols, ascorbates and mixtures thereof.

The present invention is also directed to sustained release formulations comprising cytoprotective agents and antioxidants having specially designed coatings.

The instant invention is further directed to a controlled release formulation in tablet form for once-daily oral administration of about 500–1500 mg of at least one of D-histidine, L-histidine, a racemic mixture thereof, a non-racemic mixture thereof, and nutriceutically acceptable salts thereof, which tablet comprises a homogeneous matrix comprising: about 3–12 weight percent of hydroxypropyl mehylcellulose having a number average molecular weight in the range of from about 50,000 to about 150,000; about 75–97 weight percent of at least one of D-histidine, L-histidine, a racemic mixture thereof, a non-racemic mixture thereof, and nutriceutically acceptable salts thereof in an amount effective for once daily oral administration; and about 0.05 to about 4 weight percent of a pharmaceutically acceptable lubricating agent.

DESCRIPTION OF THE PREFERRED EMBODIMENTS

The compositions of the present invention typically contain a cytoprotective agent and one or more phytonutrients having antioxidant activity. The ideal cytoprotective agent as well as antioxidant/free radical scavenger for use with the compositions of the present invention is the naturally occurring form of histidine e.g., L-histidine. However, other forms of histidine that can be used in the practice of the present invention include D-histidine, a racemic mixture thereof, a non-racemic mixture thereof, as well as pharmaceutically acceptable salts and prodrugs thereof including polyhistidine or short peptides containing effective releasable amounts of histidine. Histidine is a particularly preferred component of the nutriceutical of the present invention because it has been shown to protect cells and tissues from damage mediated by the hydroxyl radical (.OH) and singlet oxygen ($^1O_2$). Histidine is one of only a few agents that effectively scavenge singlet oxygen, a highly reactive form of molecular oxygen with an extra unpaired electron which has been shown to be an important cause of is chemical reperfusion injury. Also the favorable pharmacokinetic properties [N. G. Sitton et al, "Kinetic investigations into the possible cause of low serum histidine in rheumatoid arthritis"; *Ann. Rheum. Dis.*, 47: 48–52 (1988) and D. A. Gerber, "Determination of histidine in serum with O-Phthaldialdehyde", *Anal. Biochem.*, 34:500–504 (1970)] of histidine makes its use as an antioxidant free radical scavenger dietary supplement very attractive since it is rapidly and extensively absorbed, with maximum plasma concentrations reached one hour or less after an oral dose and bioavailability in the range of 80% to 95%.

Other amino acids such as lysine, arginine, and glycine can also be used in combination with histidine. Of course it is understood that all naturally occurring forms of the amino acids can be used in addition to other forms such as the D-forms and racemic and non-racemic mixtures.

Another important component of the nutriceutical of the instant invention are the phytonutrients. The preferred phytonutrients are those having antioxidant activity. For example, terpenes such as those found in green foods, soy products and grains, comprise one of the largest classes of phytonutrients. Terpenes of particular interest include carotenoids such as beta-carotene. The terpenes function as antioxidants, protecting lipids, blood and other body fluids from assault by free radical oxygen species including singlet oxygen, hydroxyl, peroxide and superoxide radicals. Terpenoids are dispersed widely throughout the plant kingdom, protecting plants from the same reactive oxygen species that attack human cells.

This terpene subclass consists of bright yellow, orange and red plant pigments found in vegetables such as tomatoes, parsley, oranges, pink grapefruit, spinach and red palm oil. Carotenoids also provide the bright colors seen in some animals, for example flamingos owe their color to carotenoids, as do shellfish. Egg yolks are yellow because of carotenoids that protect the unsaturated fats in the yolk.

The carotenoid family actually includes two distinct types of molecules. One type, the carotenes, are chemically classified as 40-carbon tetraterpenes, which do not include specific chemical features like hydroxyl or keto groups. This type of carotenoid includes the familiar molecule beta carotene. The second type of carotenoids, the xanthophylls, includes the chemical compounds known as the carotenoid alcohols and keto-carotenoids. In this second category are included the molecules zeaxanthin, cryptoxanthin, and astazanthin.

There are more than 600 naturally occurring carotenoids. Among the carotenes, only alpha, beta and epsilon carotene possess vitamin A activity. Of these, beta carotene is the most active. Alpha carotene possesses 50 percent to 54 percent of the antioxidant activity of beta carotene, whereas epsilon carotene has 42 percent to 50 percent of the antioxidant activity. The above-mentioned carotenes, along with gamma carotene and the carotenes, lycopene, and lutein, which do not convert to vitamin A, seem to offer protection against lung, colorectal, breast, uterine and prostate cancers (A. Bendich et al, *FASEB J* 3: 1927–32; January 1989).

Carotenes are tissue-specific in their protection. Overall protective effects are therefore greater when all carotenes are taken together. Carotenes are also known to enhance immune response and protect skin cells against UV radiation (A. Bendich, *J Nutr*, 119: 112–5 January 1989). Additionally, they spare the glutathionine Phase II detoxification enzymes in the liver that we rely on to safely eliminate pollutants and toxins from the body.

The xanthophyll type of carotenoids which can also be used in the practice of the instant invention include molecules such as canthaxantin, cryptoxanthin, zeaxanthin and astaxanthin. Xanthophylls are important because they appear to protect vitamin A, vitamin E and other carotenoids from oxidation. Evidence is also emerging that xanthophylls are tissue specific. Cryptoxanthin, for example, may be highly protective of vaginal, uterine and cervical tissues (R. S. Parker., *J Nutr*, 119: 101–4; January 1989).

The limonoids comprise another terpene subclass which can be used in the inventive compositions. The limonoids are typically found in citrus fruit peels, and their usefulness appears to be linked to protection of lung tissue. In one study, a standardized extract of d-limonene, pinene, and eucalyptol was effective in clearing congestive mucus from the lungs of patients with chronic obstructive pulmonary disease. The limonoids may also be used as specific chemopreventive agents. In animal studies, results suggest that the chemotherapeutic activity of limonoids can be attributed to induction of both Phase I and Phase II detoxification enzymes in the liver (P. Nair et al, *American Journal of Clinical Nutrition*, 40 (4 Suppl): 927–30, October 1984).

Another class of useful compounds that can be included in the compositions of the present invention include the phytosterols. The sterols occur in most plant species. Although green and yellow vegetables contain significant amounts, their seeds concentrate the sterols. Most of the research on these valuable phytonutrients has been done on the seeds of pumpkins, yams, soy, rice and herbs. Phytosterols compete with dietary cholesterol for uptake in the intestines. They have demonstrated the ability to block the uptake of cholesterol (to which they are structurally related) and facilitate its excretion from the body. It is well known that cholesterol is a significant risk factor in cardiovascular disease. However other dietary factors also play an important role. Research has shown the importance of other dietary factors in modifying the risk of cholesterol levels. A comparison of the diets of 169 Seventh Day Adventists—vegans, lacto-ovo and non-vegetarians—with general population non-vegetarians all living in Los Angeles in the mid 1980s revealed that the ratio between dietary plant phytosterols and cholesterol was significantly lower in SDA vegetarians as compared to non-vegetarians. The importance of this study underlies the fact that cholesterol, per se, is not the only marker of risk for cardiovascular disease and that its ratio with other modifying dietary components may be a better measure of risk (P. Nair, et al, *American Journal of Clinical Nutrition*, 40 (4 Suppl): 927–30, October 1984).

Other investigations have revealed that phytosterols block the development of tumors in colon, breast and prostate glands. The mechanisms by which this occurs are not well understood, but we do know that phytosterols appear to alter cell membrane transfer in tumor growth and reduce inflammation.

Other useful phytonutrients having antioxidant activity include the phenols which comprises a large class that has been the subject of extensive research as a disease preventive. Phenols protect plants from oxidative damage and perform the same function for humans. Blue, blue-red and violet colorations seen in beries, grapes and purple eggplant are due to their phenolic content. Bilberries, for example, are high in phenolic anthocyanidins and are red in color. The outstanding phytonutrient feature of the phenols is their ability to block specific enzymes that cause inflammation. They also modify the prostaglandin pathways and thereby protect platelets from clumping (M. G. Hertog et al., Lancet, 342: 1007–11, Oct. 23, 1993).

The flavonoids phytonutrients of the above phenol subclass enhance the effects of ascorbate-vitamin C. Flavonoids were once lumped together as vitamin P, but there are well over 1,500 of them. Among the most useful flavonoids which can be used in the practice of the instant invention there are included the flavones (containing the flavonoid apigenin found in chamomile); Flavonols (quercetin—grapefruit; rutin—buckwheat; ginkgoflavonglycosides—ginkgo); Flavanones (hsperidin—citrtis fruits; silybin—milk thisle). The biologic activities of flavonoids include action against allergies, inflammation, free radicals, hepatotoxins, platelet aggregation, microbes, ulcers, viruses and tumors (J. E. Kinsella et al., Food Technology, 47: 85–90, April 1993). Flavonoids also inhibit specific enzymes. For example, flavonoids block the angiotensin-converting enzyme (ACE) that raises blood pressure: By blocking the suicide enzyme cyclooxygenase that breaks down prostaglandins, they prevent platelet stickiness and hence platelet aggregation. Flavonoids also protect the vascular system and strengthen the tiny capillaries that carry oxygen and essential nutrients to all cells (J. E. Kinsella et al., Food Technology, 47: 85–90, April 1993). Additionally, flavonoids block the enzymes that produce estrogen, thus reducing the risk of estrogen-induced cancers. One way they do this is by blocking estrogen synthase, an enzyme that binds estrogen to receptors in several organs (C. Northrup, Women's Bodies, Women's Wisdom: 305. New York; Bantam Books, 1994). Although their way of doing so is not yet fully understood, flavonoids also appear to retard development of cataracts in individuals with inborn errors in sugar metabolism such as diabetes (R. K. Murray et al., Harper's Biochemistry, 23 ed.: 196. New York; Appleton and Lange, 1994). Cataracts can be a complication of diabetes because diabetics, unable to metabolize sugar normally, build up damaging levels of alcohol sugars. These in turn cause clouding of the lens of the eye (cataract). It is suspected flavonoids prevent cataracts by blocking aldose-reductase (a digestive enzyme), which can convert the sugar galactose into the potentially harmful form of galacticol. This select group of flavonoids deserves special attention. Technically known as flavonals; they provide crosslinks or bridges; that connect and strengthen the intertwined strands of collagen protein. Collagen is the most abundant protein in the body, making up soft tissues, tendons, ligaments and bone matrix. Its great tensile strength depends on preservation of its crosslinks.

Anthocyanidins, being water soluble, also scavenge free radicals they encounter in tissue fluids. This is a powerful ability especially beneficial for athletes and others who exercise, because heavy exercise generates large amounts of free radicals.

Catechins differ slightly in chemical structure from other flavonoids, but share their chemoprotective properties. The most common catechins are gallic esters, named epicatechin (EC), epicatechin gallate (ECG), and epigallocatechin gallate (EGCG). All are found in green tea, Camellia sinensis, and are thought to be responsible for the protective benefits of this beverage (C. I. Xie et al., Alcohol Clin Exp Res, 18: 1443–7, December 1994).

The isoflavones type of phytonutrients also included within the phenol subclass come from beans and other legumes and are distant cousins of flavonoids. Isoflavones function much like flavonoids in that they effectively block enzymes that promote tumor growth. The most useful isoflavones that can used in formulating the compositions of the present invention are genistein and daidzein found in soy products and the herb Pueraria lobata (Kudzu). People who consume traditional diets rich in soy foods rarely experience breast, uterine and prostate cancers. Pueraria has gained popularity as an aid for those who consume alcohol because it appears to alter the activity of alcohol detoxification enzymes, namely the speed at which alcohol dehydrogenase converts alcohol into aldehydes. The result is a lowered tolerance for alcohol and reduction of the pleasure response to drinking it. Phytonutrients of this sulfur-containing class are present in garlic and cruciferous vegetables (i.e., cabbage, turnips and members of the mustard family). Found in cruciferous vegetables, glucosinolates are powerful activators of liver detoxification enzymes. They also regulate white blood cells and cytokines (Y. Zhang et al., Proc Natl Acad Sci USA,. 91: 3147–50, Apr. 12, 1994). White blood cells are the scavengers of the immune system and cytokines act as messengers; coordinating the activities of all immune cells.

Another type of flavonoids that can be used in the practice of the present invention is known as oligomeric proanthocyanidins (OPC's). They occur in most plants, are highly bioavailable and are active in the body as tremendous antioxidants and free radical scavengers. OPC's are chemically classified as flavanols and are present in red wines, flowers, leaves, fruits, berries, nuts, sorghum, beans and hops with high concentrations in skins, barks and seeds. The most feasible commercial source is the seeds of grapes and the bark of the French Maritime pine. Technically speaking, OPC's are really not bioflavonoids. OPC's are "flavanols" while bioflavonoids are "flavonoids." While the chemical structure of their core molecules is the same, flavonols and flavonoids actually have more differences than similarities. OPC's are colorless, bioflavonoids are yellow. OPC's are water soluble, bioflavonoids are relatively insoluble. Flavanols, including OPC's, are always made up of polymers of one compound called "flavan-3-ol", while bioflavonoids are made up of many different compounds with a "flavane" nucleus. U.S. Pat. No. 4,698,360 whose entire contents are incorporated by reference herein discloses the use of OPC's as antioxidants to protect the body against the harmful biological effects of free radicals. According to the '360 patent, OPC'S are known to cross the blood brain barrier and improve oxygenation of brain tissue, which may be helpful in treating attention deficit syndrome. OPC's are one of the most prevalent compounds that occur in natural whole foods. Up to 25% of OPC extract consists of monomeric precursors, the building blocks of OPC. In grape seed extract, these precursors are known as catechins and epicatechins. Pine bark extract contains catechins and taxifolin.

Every plant species has its own unique precursor mix. Blending both grape seed and pine bark extracts combines all their monomeric precursors. The two together provide a broad spectrum, creating a more complete storehouse of OPC building blocks. On their own, these precursors are inactive and short lived. However, catalyzed by the presence of OPC, they become active and unfurl their own unique biological benefits rendering the blend richer in total activity.

OPC'S are probably the most versatile nutrients ever discovered. They are the most active free radical scavenging antioxidants known. They help protect against all degenerative conditions, such as cancer, cardiovascular diseases, stroke, allergies and aging. OPC's, or proanthocyanidins are the most powerful antioxidant free radical scavengers known to man. They are as much as 50 times more potent than vitamin E and 20 times more than vitamin C. OPC,s are major protectors of collagen, the basic foundation our blood vessels and all connective tissues such as skin, ligaments around joints and tendons.

Additional compounds that can be used also include the bio-transformation products of glucosinolates which include isothiocyanates, dithiolthiones and sulforaphane. Each of these is protective of specific tissues. Their actions involve blocking enzymes that promote tumor growth, particularly in the breast, liver, colon, lung, stomach and esophagus (P. P. Tadi, Diss Abstr Int (B), 52: 4144, 1992). Garlic and onions are the most potent members of this thiol subclass, which also includes leeks, shallots and chives. The allylic sulfides in these plants are released when the plants are cut or smashed. Once oxygen reaches the plants cells, various bio-transformation products are formed. Each of these appears to have tissue specificity. As a group, allylic sulfides appear to possess antimutagenic and anticarcinogenic properties as well as immune and cardiovascular protection. They also appear to offer anti-growth activity for tumors, fungi, parasites, cholesterol and platelet/leukocyte adhesion factors. Garlic and onions, like their cruciferous relatives, can also activate liver detoxification enzyme systems. Certain allylic sulfides are known to block the activity of toxins produced by bacteria and In viruses (P. P. Tadi, Diss Abstr Int (B), 52: 4144, 1992).

The indole subclass of phytonutrients can also be added to the compositions of the present invention because of their interaction with vitamin C, which is not surprising since the vegetables that contain indoles also contain significant amounts of vitamin C. Indole complexes bind chemical carcinogens and activate detoxification enzymes, mostly in the gastrointestinal tract. The bio-transformation products of indoles are formed when they are acted on by stomach acid. The most active product is ascorbigen, considered to be an active vitamin C metabolite (V. M. Bukhman et al, Pharmacol Ther, 60: 301–313, 1992).

An additional family of compounds which are also useful for addition to applicants compositions include the Isoprenoids which are known to neutralize free radicals in a unique way. They have a long carbon side chain which they use to anchor themselves into fatty membranes. Any free radicals attempting to attach lipid (fat) membranes are quickly grabbed and passed off to other antioxidants.

A particularly preferred family of antioxidants to be combined with the other components of the present invention are the tocotrienols and the tocopherols. The tocotrienols naturally occur in grains and palm oil along with their cousins, the tocopherols. Toco-trienols appear to inhibit breast cancer cell growth, whereas tocopherols do not exhibit this effect. Researchers have observed that the biologic functions of tocopherols and tocotrienols appear unrelated (K. C. Hayes et al., Exp Biol Med, 202: 353–359, March 1993). Tocotrienols have been most studied, however, for their cholesterol lowering effects.

The tocopherols are also particularly important. Vitamin E comprises a group of natural substances known as tocopherols. These are fat soluble, closely related chemical compounds found in vegetable oils such as wheat germ oil, soybean oil and the like. α-tocopherol has the greatest biological activity while its homolog have vitamin E activity to a lesser extent. The vitamin E can be incorporated either as the free tocopherol or as the esters i.e., d-α-tocopheryl acid succinate. Of course, the racemic and nonracemic mixtures may also be used.

Lipoic acid and ubiquinone are further additives which can be incorporated in the inventive compositions. Lipoic acid and ubiquinone (coenzyme Q) are important antioxidants that work to extend the effects of other antioxidants. Lipoic acid is known to be an efficient hydroxyl radical quencher, its sulfur bond being the reactive part of the molecule. It is active on both lipids and tissue fluids. In addition to hydroxyl radicals, it scavenges peroxyl, ascorbyl and chromanoxyl radicals. Because it functions in both lipid and water phases, it is protective of both vitamin E and vitamin C. Lipoic acid also protects SOD, catalase and glutathione, which are all important in liver detoxification activities (R. Sumathi et al., Pharmacol Res, 27: 309–318, May–June 1993). The roles of both lipoic acid and ubiquinone as antioxidants have been discovered relatively recently. Both have important roles in energy production.

Another preferred antioxidant of particular interest to be used in the compositions of the present invention is vitamin C. The vitamin C can be in the form of the acid or as sodium ascorbate or in other biologically acceptable mineral form such as calcium ascorbate, magnesium ascorbate, zinc ascorbate, iron ascorbate and others. Of course the ascorbic acid can also be introduced in the form of a pro-drug e.g, as an ester which will hydrolyze into an inert acid and ascorbic acid i.e., ascorbyl palmitate and other fatty acid esters.

The amount of the nutriceuticals to be used in dosage forms can be any amount that is considered safe for human consumption and approved by the acceptable guidelines promulgated by the Food and Drug Administration. For humans, typically effective amounts of histidine for use in the unit dose compositions of the present invention range from 50 mg to 32g per 24 hours (0.7 to 450 mg/kg/day ); however, greater amounts may be employed if desired. This range is based on administration to a 70 Kg human. A preferred amount is 100 to 1500 mg per 24 hour period. Of course, the amounts of each compound selected will depend on the weight of the mammal and the levels of cytoprotection, free radical scavenging effect and antioxidant activity that are needed. One skilled in the art can adjust the dosage forms to achieve the desired therapeutic levels. Because of histidine's favorable safety profile, large doses can also be administered in the nutriceutical of the present invention. In humans, acute oral doses of up to 32 g/day (450 mg/kg/day ) of histidine have not been associated with any adverse effects, and only mild, reversible effects were observed with acute doses up to 64 g/day.

The amount of vitamin C and other antioxidants which can be combined with histidine is typically in the range of 0.0001 to 10 times the amount of histidine. Of course in some cases such as with the fat soluble antioxidants i.e., vitamin A, vitamin E and beta-carotene, their amounts are chosen according to the National Research Council's Recommended Dietary Allowances. Typically, for vitamin A, the adult requirement is based on body weight and is 20 International units (IU) of retinol/Kg (one international unit equals 0.30 mcg of trans-retinol or 0.344 mcg of trans-retinol acetate. Provitamin A is required in the amount of 40 IU/kilogram (one IU of provitamin A equals 0.6 mcg of β-carotene). For vitamin E, the amounts will typically range from 5 to 100 mg of β-tocopherol although higher amounts are possible as long as that higher amount is not a toxic dosage. For purposes of the present invention 1IU=lmg of d,l α-tocopheryl acetate=0.91 mg d,l α-tocopherol=0.735 mg d α-tocopheryl acetate=0.671 mg d α-tocopherol.

The nutriceuticals of the present invention can also be combined with all of the traditional vitamin supplements. For example, histidine and all the antioxidants listed above can be formulated with the following additional ingredients: Vitamin A, vitamin A acetate, vitamin $B_1$, vitamin $B_2$, vitamin $B_6$, vitamin $B_{12}$, vitamin D, calcium panthotenate, niacinamide, copper, iodine, iron, magnesium, manganese, zinc, folic acid, iron, thiamine mononitrate, riboflavin, pyridoxine hydrochloride and selenium. The above metals are typically incorporated either as the sulfates or as the carbonates.

The preferred compositions of the present invention can be prepared and administered in a wide variety of oral, topical and parenteral dosage forms. It will be obvious to those skilled in the art that the following dosage forms may comprise as the component, either histidine alone or in combination with other phytonutrients having antioxidant activities.

Preferably the compounds of the present invention are administered orally, cutaneously, intramuscularly, subcutaneously, or intravenously. Oral rehydration solutions are also contemplated in the practice of the present invention.

For preparing nutriceutical compositions from the compounds of the present invention, nutriceutical acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants suspending agents, binders, preservatives, tablet disintegrating agents, or an encapsulating material.

In powders, the carrier is a finely divided solid which is in a mixture with the finely divided nutriceutically active component.

In tablets, the nutriceutically active component is mixed with the carrier having the necessary binding properties in suitable proportions and compacted in the shape and size desired.

The powders, capsules and tablets preferably contain from five or ten to about seventy percent of the nutriceutical composition. Suitable carriers are magnesium carbonate, magnesium stearate, talc, sugar, lactose, pectin, dextrin, starch gelatin, tragacanth, methylcellulose, sodium carboxymethylcellulose, a low melting wax, cocoa butter, and the like. The term "preparation" is intended to include the formulation of the nutriceutical composition with encapsulating material as a carrier providing a capsule in which the active component, with or without other carriers, is surrounded by a carrier, which is thus in association with it. Similarly, cachets and lozenges are included. Tablets, powders, capsules, soft gelatin shells, pills cachets, and lozenges can be used as solid dosage forms suitable for oral administration. Lotions, ointments, or suspensions can be used as dosage forms for topical application. Anti-aging lotions, creams and onitments which also include alpha and beta hyrdoxy acids are also contemplated within the scope of the present invention.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid for preparations include solutions, suspension, emulsions, for example, water or water propylene glycol solutions or DMSO solutions. For parenteral injection, liquid preparations can be formulated in solution in aqueous polyethylene glycol solution or DMSO-water solutions.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid for preparation for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Oral rehydration solutions containing histidine are also contemplated by the present invention.

The nutriceutical preparation is preferably in unit dosage form. In such form, the preparation is subdivided into unit doses containing appropriate quantities of the nutriceutically active component. The unit dosage form can be a packaged preparation, the package containing discrete quantities of preparation, such as packeted tablets, capsules, lotions, ointments and powders in vials or ampoules. Also, the unit dosage form can be a drink, capsule, tablet, cachet, lotion, ointment, or lozenge itself, or it can be the appropriate number of any of these in packaged form.

When making soft gelatin shells, the shell typically consists of 20 to 70 percent gelatin, generally a plasticizer and 5 to 60% by weight sorbitol. The filling of the soft gelatin capsule is liquid and includes, apart form the antioxidant actives, a hydrophilic matrix. Typically such hydrophilic matrix comprises polyethylene glycol having an average molecular weight of from about 200 to 1000. Further ingredients are water and optionally thickening agents. It is preferred that the hydrophilic matrix includes polyethylene glycol having an average molecular weight of from about 200 to 1000, 5 to 15% glycerol, and 5 to 15% by weight of water. The polyethylene glycol can also be mixed with propylene glycol andlor propylene carbonate.

In a preferred embodiment, there is provided a dosage unit form of the soft gelatin shell with a filling of histidine and the other antioxidants contemplated by the invention in combination with a hydrophilic matrix comprising polyethylene glycol having an average molecular weight of from about 200 to 1000, or a mixture of the polyethylene glycol with propylene glycol, glycerol in 5 to 15% by weight, and water in 5 to 15% by weight.

As for the manufacturing, it is contemplated that standard soft shell gelatin capsule manufacturing techniques will be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

The present invention also provides a new controlled release oral tablet for once a day administration of 500–1500 mg of D-histidine, L-histidine, a racemic mixture thereof, a non-racemic mixture thereof, and nutriceutically acceptable salts thereof, which tablet comprises a homogeneous matrix comprising: about 3–12 weight percent of hydroxypropylmethylcellulose having a number average molecular weight in the range of from about 50,000 to about 150,000; about 75–97 weight percent of D-histidine, L-histidine, a racemic mixture thereof, a non-racemic mixture thereof, and nutriceutically acceptable salts thereof, in an amount effective for once daily oral administration; and about 0.05 to about 4 weight percent of a pharmaceutically acceptable lubricating agent.

The tablet matrix includes a minor amount of a pharmaceutically acceptable lubricating agent such as magnesium stearate to aid in the tableting process. This amount will vary between about 0.05 and 4% generally, and preferably represents about 1% of the total weight of the tablet. Suitable tablet lubricants include magnesium stearate, stearic acid, calcium stearate and the like, or mixtures thereof. Magnesium stearate is preferred.

Optionally, the tablet matrix may include minor amounts of other pharmaceutically acceptable excipients such as colorants and glidants. Suitable colorants include, but are not limited to, FD & C Yellow #5, FD&C Yellow #6, and FD&C Blue #2, and generally represent 1% or less of the tablet weight. Suitable glidants include, but are not limited to, pharmaceutical grades of talc and fused silica, and generally represent 7% or less of the tablet weight.

The term matrix, as used herein, refers to a uniform mixture of D-histidine, L-histidine, a racemic mixture thereof, a non-racemic mixture thereof, and nutriceutically acceptable salts thereof, hydroxypropyl methylcellulose, a lubricating agent, and other optionally included excipients. An important aspect of the present invention is the fact that the hydroxypropyl methylcellulose is uniformly dispersed throughout the matrix to achieve uniform drug release. The matrix may be made by any pharmaceutically acceptable technique which achieves uniform blending, including dry blending, conventional wet granulation, compression granulation, and fluid-bed granulation. Tablets can be made from the resulting matrix by any known tableting technique.

In accordance with the present invention, the amount of D-histidine, L-histidine, a racemic mixture thereof, a non-racemic mixture thereof, and nutriceutically acceptable salts thereof, that is incorporated in a tablet may range between about 500 and about 1500 mg. The tablet of the present invention provides a release period suitable for once-daily dosing, i.e. once within a 24 hour period. Generally, D-histidine, L-histidine, a racemic mixture thereof, a non-racemic mixture thereof, and nutriceutically acceptable salts thereof, are administered at levels of 500, 750, 1000 or 1500 mg/day.

The hydroxypropylmethylcellulose utilized in the present invention is a water soluble cellulose ether, and is commercially available in various grades under the tradenames Methocel Premium K4M, A4M, E4M and F4M (Dow Chemical Co., U.S.A.) which are 4000 cps viscosity polymers having number average molecular weights in the range of 85,000–95,000, and Methocel K15M, a 15,000 cps viscosity polymer having a number average molecular weight in the range of 120,000–130,000. Other suitable polymers include Metolose SM, 60SH, 65SH, and 90SH, viscosity grades 4000, 8000, 15,000 and 30,000 available from Shin-Etsu Ltd., Japan. Specific preferred hydroxypropyl methylcelluloses are Methocel K4M Premium and Methocel K15M Premium.

The physicochemical properties of these polymers vary over a wide range. Preferred embodiments of this invention utilize premium grade polymers of a single viscosity type having number average molecular weights in the range of about 50,000–150,000. However, a mixture of two or more grades or viscosity types resulting in number average molecular weights in the range of about 50,000–150,000 can be used.

The number average molecular weight of the hydroxypropyl methylcellulose which is used in the tablet matrix substantially influences the release profile which is obtained. The number average molecular weight (Mn) is the sum of the individual molecular weights of a representative sample population of molecules divided by the number of molecules in that sample, and is calculated from the limiting osmotic pressure of the solvent as the concentration of the hydroxypropyl methylcellulose approaches zero. The hydroxypropyl methylcellulose must have a number average molecular weight in the range of from about 50,000 to about 150,000, preferably from about 125,000 to about 135,000. When the polymer has a number average molecular weight of 125,000–135,000, it constitutes preferably about 3–12 weight percent of a 750 to 1000 mg L-Histidine controlled release tablet, or about 7 weight percent of a 500 to 750 mg L-Histidine controlled release tablet. A second preferred range of number average molecular weight of the hydroxypropyl methylcellulose is about 85,000 to about 95,000. When the polymer has a number average molecular within this range, it constitutes preferably about 7–9 weight percent of the controlled release L-Histidine tablet.

Optionally, the controlled release tablets may be coated with any conventional or non-conventional coating which is pharmaceutically acceptable. Generally, the coatings will be applied for such purposes as product identification, printability of the tablet, light protection, aesthetic appearance and patient compliance, and will not effect the release rate profile of the tablet. Conventional coating formulations which may be used include aqueous and solvent-based polymeric, gum and cellulose-based films, as well as sugar coatings. Numerous pharmaceutically acceptable coating formulations have been developed by the pharmaceutical industry and are well known to the pharmaceutical scientist.

Exemplary of typical film coating materials are formulations of such film forming agents as polyvinylpyrrolidone, acrylic polymers and copolymers, natural gums and resins, low molecular weight hydroxypropyl methylcellulose, hydroxypropyl cellulose, ethyl cellulose and methylcellulose. These formulations may include plasticizing agents such as acetylated monoglycerin, castor oil, mineral oil, glycerol, diethyl phthalate, triethylcitrate, triacetin, glycerin, propylene glycol, polyethylene glycol, and the like, as well as surface active agents such as polysorbates, colorants, and opacifiers such as titanium dioxide and talc.

A preferred coating formulation for the tablets of this invention comprises a mixture of low molecular weight hydroxypropyl methylcellulose and polyethylene glycol. Such coatings are readily formulated by standard means well known to the pharmaceutical chemist, and are also commercially available. Exemplary of a commercially available coating material suitable for application to the tablets of this invention is Opadry RTM., a low molecular weight hydroxypropyl methylcellulose/polyethylene glycol material available from Colorcon.

The controlled release tablets of the present invention provide nutriceutically effective blood levels of L-Histidine for at least 12 to 24 hours, and are thus suitable for once-daily administration. Fluctuations in blood levels during multi-dose therapeutic regimens are minimized by the tablets of the present invention.

The examples described below are presented for illustration purposes only and are not intended to limit the scope of the invention of this application which is defined in the claims. The present invention is further explained more specifically with reference to the following formulation examples without limit thereto. The parts and percentages in the formulation Examples are represented by weight:

EXAMPLE I

The following example illustrates a histidine formulation which can be made into a capsule:

| COMPONENT | AMOUNT |
| --- | --- |
| Histidine | 250 mg |
| Lactose | q.s to selected size |

The active ingredients are triturated and q.s. with lactose to selected capsules size.

EXAMPLE II

| COMPONENTS | AMOUNT |
| --- | --- |
| Histidine | 125 mg |
| Vitamin C | 125 mg |
| Vitamin E | 75 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE III

| COMPONENTS | AMOUNT |
| --- | --- |
| Histidine | 350 mg |
| Vitamin C | 145 mg |
| β-Carotene | 5000 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE IV

| COMPONENTS | AMOUNT |
| --- | --- |
| Histidine | 400 mg |
| Vitamin E | 50 I.U. |
| β-Carotene | 4500 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE V

| COMPONENTS | AMOUNT |
| --- | --- |
| Histidine | 285 mg |
| Vitamin A | 1700 I.U. |
| β-Carotene | 5000 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE VI

| COMPONENTS | AMOUNT |
| --- | --- |
| Histidine | 250 mg |
| Vitamin C | 245 mg |
| β-Carotene | 2500 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE VII

| COMPONENTS | AMOUNT |
| --- | --- |
| Histidine | 300 mg |
| Vitamin A | 850 I.U. |
| β-Carotene | 5000 I.U. |
| Vitamin C | 200 mg |
| Vitamin E | 70 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE VIII

| COMPONENTS | AMOUNT |
| --- | --- |
| Histidine | 200 mg |
| Vitamin A | 2000 I.U. |
| β-Carotene | 3000 I.U. |
| Magnesium sulfate | 100 mg |
| Vitamin C | 175 mg |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE IX

Hard gelatin capsules are prepared using the following ingredients:

| COMPONENT | mg/Capsule |
| --- | --- |
| Histidine | 250 |
| Starch dried | 200 |
| Magnesium Stearate | 10 |

The above ingredients are mixed and filled into hard gelatin capsules in 460 mg quantities.

EXAMPLE X

A tablet formula is prepared using the ingredients below:

| COMPONENT | mg/Tablet |
| --- | --- |
| Histidine | 150 |
| Vitamin C | 100 |
| Microcrystalline cellulose | 400 |
| Fumed Silicon Dioxide | 10 |
| Stearic Acid | 5 |

The components are blended and compressed to form tablets each weighing 665 mg.

EXAMPLE XI

Tablets each containing 60 mg of active ingredients are made up as follows:

| COMPONENT | mg/Tablet |
| --- | --- |
| Histidine | 20 |
| Vitamin C | 20 |
| Vitamin E in dry carrier | 20 |
| Starch | 45 |
| Microcrystalline Cellulose | 35 |
| Polyvinylpyrrolidone (as 10% solution in water) | 4.0 |
| Sodium Carboxymethyl starch | 4.5 |
| Magnesium stearate | 0.5 |
| Talc | 1.0 |

The nutriceutically active ingredients, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE XII

Capsules each containing 80 mg of nutriceuticals are made as follows:

| COMPONENTS | mg/Capsule |
| --- | --- |
| L-Histidine | 30 mg |
| Vitamin C | 35 mg |
| Vitamin E | 14 mg |
| β-Carotene | 1 mg |
| Starch | 59 mg |
| Microcrystalline Cellulose | 59 mg |
| Magnesium Stearate | 2 mg |

The nutriceutical active ingredients, cellulose, starch and magnesium stearate are blended, passed through a No. 45 mesh U.S. sieve, and filled into hard gelatin capsules in 200 mg quantities.

EXAMPLE XIII

Suspensions each containing 50 mg of histidine per 5 ml dose are made as follows:

| COMPONENT | AMOUNT |
| --- | --- |
| L-Histidine | 50 mg |
| Sodium Carboxymethyl cellulose | 50 mg |
| Syrup | 1.25 ml |
| Benzoic Acid solution | 0.10 ml |
| Flavor | q.v. |
| Color | q.v |
| Purified water | to 5 ml |

The histidine is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

EXAMPLE XIV

Suspensions each containing 25 mg of histidine and 25 mg of vitamin C per 5 ml dose are made as follows:

| COMPONENT | AMOUNT |
| --- | --- |
| L-Histidine | 25 mg |
| Vitamin C | 25 mg |
| Sodium Carboxymethyl cellulose | 50 mg |
| Syrup | 1.25 ml |
| Benzoic Acid solution | 0.10 ml |
| Flavor | q.v. |
| Color | q.v |
| Purified water | to 5 ml |

The histidine and vitamin C are passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

EXAMPLE XV

Capsules each containing 150 mg of nutriceuticals are made as follows:

| COMPONENT | mg/Capsule |
|---|---|
| Histidine | 50 mg |
| Vitamin C | 50 mg |
| Vitamin E | 45 mg |
| Vitamin A | 4 mg |
| β-Carotene | 1 mg |
| Starch | 164 mg |
| Microcrystalline Cellulose | 164 mg |
| Magnesium Stearate | 22 mg |

The active ingredient, cellulose, starch and magnesium stearate are blended, passed through a No. 45 mesh U.S. sieve, and filled into hard gelatin capsules in 500 mg quantities.

EXAMPLE XVI

Example XV is repeated except one microgram of selenate is added to the formulation.

EXAMPLE XVII

SUSTAINED RELEASE COMPOSITION CONTAINING HISTIDINE 350 grams of histidine crystals, all having a size of between 20 and 70 mesh, are placed in a six inch air suspension coating column (Wurster column of manufacture by Glatt, West German) and coated with a mixture of 184 ml polymer solution in chloroform which contained 15 gm ethylcellulose ["Ethocel N-10" (Dow)] and 3.7 gm hydroxypropyl cellulose ["Klucel LF" (Hercules)] and 46 ml of methanol. The coating solution is sprayed at 2.5 bar pressure with the liquid feed rate of 30 ml/minute. The inlet air temperature is about 60° C. After completion of the feed of the coating, the quickly dried polymerically coated histidine crystals are recovered from the bottom of the air suspension coating column.

EXAMPLE XVIII

SUSTAINED RELEASE COMPOSITION CONTAINING HISTIDINE AND VITAMIN C 350 grams of histidine crystals and 350 grams of vitamin C crystals, all having a size of between 20 and 70 mesh, are placed in a six inch air suspension coating column (Wurster column of manufacture by Glatt, West German) and coated with a mixture of 368 ml polymer solution in chloroform which contained 30 gm ethylcellulose ["Ethocel N-10" (Dow)] and 7.4 gm hydroxypropyl cellulose ["Klucel LF" (Hercules)] and 92 ml of methanol. The coating solution is sprayed at 2.5 bar pressure with the liquid feed rate of 60 ml/minute. The inlet air temperature is about 60° C. After completion of the feed of the coating, the quickly dried polymerically coated histidine and vitamin C crystals are recovered from the bottom of the air suspension coating column.

EXAMPLE XIX

Sustained release tablets containing L-Histidine are made as follows: 3500 gms of L-histidine and 180 gms Methocel K15M were well blended, and then granulated with about 1000 ml of purified water. The granulation was tray dried in a 50 degree. C. oven for 16 hours, passed at slow speed through a hammer mill fitted with an 18 gauge screen, and then thoroughly mixed with 39 gms of magnesium stearate. The resulting homogeneous matrix material was compressed into tablets of about 800 mg in weight and size.

The following represent additional formulation examples:

EXAMPLE XX

| COMPONENTS | AMOUNT |
|---|---|
| Histidine | 250 mg |
| Vitamin C | 245 mg |
| lycopene | 2500 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE XXI

| COMPONENTS | AMOUNT |
|---|---|
| Histidine | 250 mg |
| lycopene | 2500 I.U. |
| Anhydrous glycerol | 35 mg |
| Polyethylene glycol 400 | 315 mg |

The above components are thoroughly mixed under a nitrogen atmosphere, and are then encapsulated in conventional soft gelatin shells.

EXAMPLE XXII

| COMPONENTS | AMOUNT |
|---|---|
| Histidine | 250 mg |
| Lipoic acid | 0.1 mg |
| Anhydrous glycerol | 35 mg |
| Polyethylene glycol 400 | 315 mg |

The above components are thoroughly mixed under a nitrogen atmosphere, and are then encapsulated in conventional soft gelatin shells.

Various other examples and modifications or adaptations of the foregoing Examples can be devised by a person skilled in the art after reacting the foregoing specification and the appended claims without departing from the spirit and scope of the invention. All such further Examples, modifications and adaptations are included within the scope of the invention.

It will be appreciated by those versed in the art, that the present invention makes available novel and useful nutriceutical compositions having cytoprotective effects in several administration forms including sustained release. Also, it will be understood by those with knowledge in the nutriceutical art, that many embodiments of this invention may be made without departing from the spirit and scope of the invention, and the invention is not to be construed as limited, as it embraces all equivalents therein.

What is claimed is:

1. A dietary supplement comprising:
   (a) an effective amount of a synthetic or naturally occurring phytonutrient selected from the group consisting of canthanaxin, limonene and vitamin A;
   (b) a cytoprotective effective amount of histidine wherein said histidine is selected from the group consisting of at least one of D-histidine, L-histidine, a racemic mixture thereof, a non-racemic mixture thereof, and nutriceutically acceptable salts thereof, and a nutriceutically inert carrier selected from the group consisting of microcrystalline cellulose, polyethylene glycol, sodium carboxymethyl cellulose and hydroxypropyl methylcellulose.

2. A nutricoutical histidine composition comprising:
   (a) an effective cyto-protective amount of histidine wherein said histidine is selected from the group consisting of at least one of D-histidine, L-histidine, a racemic mixture thereof, a non-racemic mixture thereof, and nutriceutically acceptable salts thereof;
   (b) an effective amount of one or more of a phytonutrient having antioxidant activity selected from the group consisting of canthaxantin, limonene, vitamin A and mixtures thereof; and
   (c) a nutrceutically inert carrier selected from the group consisting of microcrystalline cellulose, polyethylene glycol, sodium carboxymethyl cellulose and hydroxypropyl methylcellulose.

3. A method of providing nutrition to a mammal in need thereof, which method comprises administering to said mammal a composition comprising:
   (a) an effective amount of a cyto-protective agent selected from the group consisting of at least one of D-histidine, L-histidine, a racemic mixture thereof, a non-racemic mixture thereof, and nutriceulically acceptable salts thereof; and
   (b) an effective amount of at least one of a phytonutrient having antioxidant activity selected from the group consisting of canthaxantin, limonene, vitamin A and mixtures thereof.

* * * * *